(12) United States Patent
Wright et al.

(10) Patent No.: US 7,815,671 B2
(45) Date of Patent: *Oct. 19, 2010

(54) CONTROLLED DEPLOYMENT DELIVERY SYSTEM

(75) Inventors: Michael Wright, Allen, TX (US); Timothy Lostetter, Cooper City, FL (US); Alex Ruiz, Miami, FL (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 427 days.

This patent is subject to a terminal disclaimer.

(21) Appl. No.: 11/829,503

(22) Filed: Jul. 27, 2007

(65) Prior Publication Data

US 2008/0021538 A1    Jan. 24, 2008

Related U.S. Application Data

(63) Continuation of application No. 10/455,978, filed on Jun. 5, 2003, now Pat. No. 7,264,632.

(60) Provisional application No. 60/387,278, filed on Jun. 7, 2002.

(51) Int. Cl.
    *A61F 2/06*    (2006.01)
(52) U.S. Cl. .................... 623/1.12; 623/1.11; 623/1.23
(58) Field of Classification Search ....... 623/1.11–1.14, 623/1.23; 606/198, 108, 191, 192, 194
    See application file for complete search history.

(56) References Cited

U.S. PATENT DOCUMENTS

| | | | |
|---|---|---|---|
| 5,391,172 A | 2/1995 | Williams et al. | |
| 5,458,615 A * | 10/1995 | Klemm et al. | 606/198 |
| 5,824,041 A * | 10/1998 | Lenker et al. | 606/195 |
| 5,902,334 A | 5/1999 | Dwyer et al. | |
| 5,919,204 A | 7/1999 | Lukic et al. | |
| 6,077,297 A | 6/2000 | Robinson et al. | |
| 6,395,017 B1 * | 5/2002 | Dwyer et al. | 623/1.11 |
| 6,858,034 B1 | 2/2005 | Hijlkema et al. | |
| 6,890,337 B2 | 5/2005 | Feeser et al. | |
| 7,004,964 B2 | 2/2006 | Thompson et al. | |
| 7,264,632 B2 * | 9/2007 | Wright et al. | 623/1.12 |
| 2003/0135162 A1 | 7/2003 | Deyette et al. | |

FOREIGN PATENT DOCUMENTS

| | | |
|---|---|---|
| FR | 2779939 | 6/1998 |
| WO | WO 01/17458 | 3/2001 |

\* cited by examiner

*Primary Examiner*—Eduardo C Robert
*Assistant Examiner*—Christopher Schubert

(57) ABSTRACT

A controlled stent-graft deployment delivery system (10 50 or 900) includes a stent-graft (30 or 63), a retractable primary sheath (40) containing the stent-graft in a first constrained diameter configuration, an outer tube (18) within the retractable primary sheath and within the stent-graft, and an inner tube (20) within the outer tube, where the inner tube and the outer tube both axially move relative to the retractable primary sheath and to each other. The system further includes a cap (15) coupled to a distal end of the inner tube and configured to retain at least a portion of a proximal area of the stent-graft in a radially compressed configuration. A distal assembly (100) provides controlled relative axial movement between the outer tube and the inner tube enabling the release of the proximal end (65, 67, 68, and 69) of the stent-graft from the cap and from the radially compressed configuration.

6 Claims, 6 Drawing Sheets

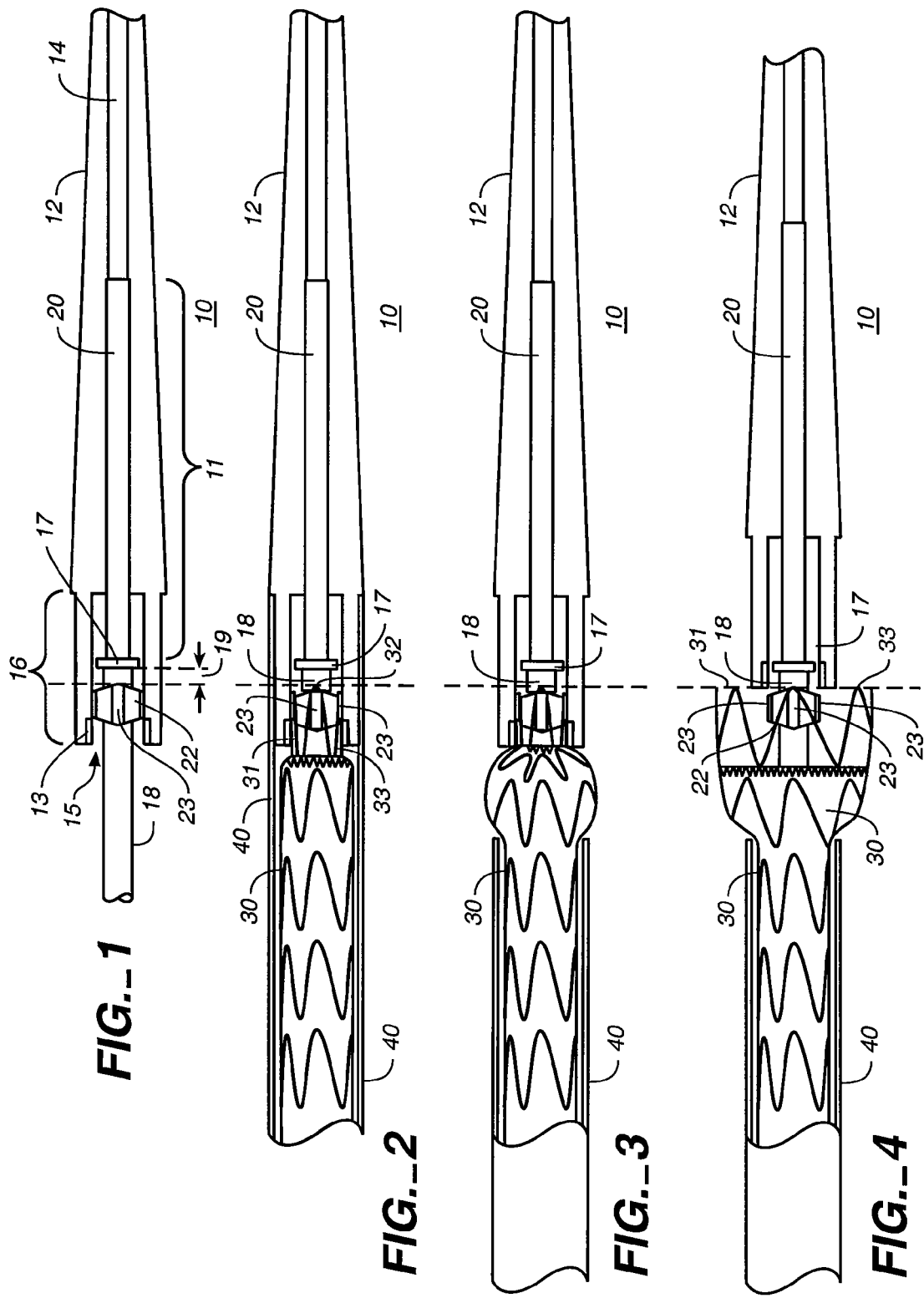

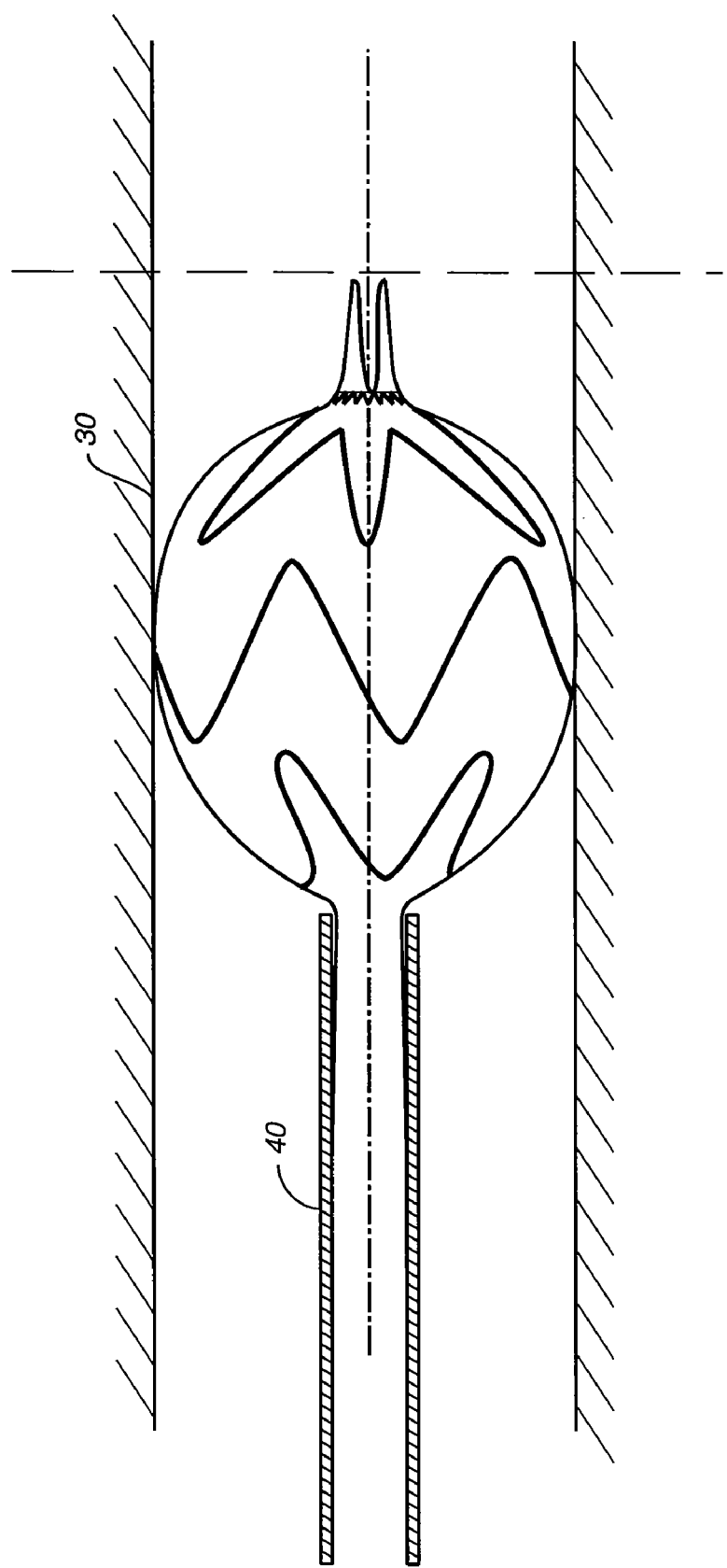

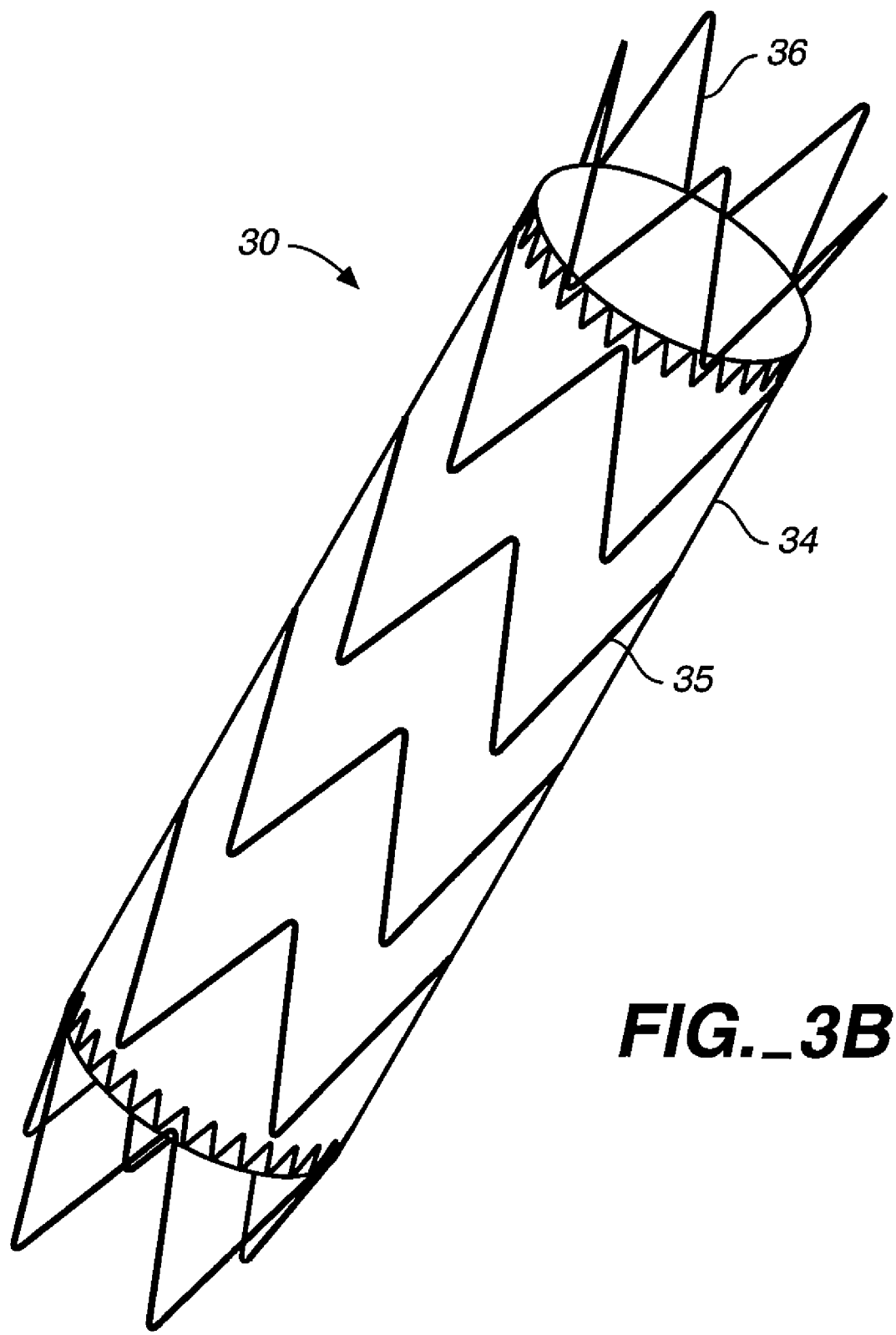
FIG._3B

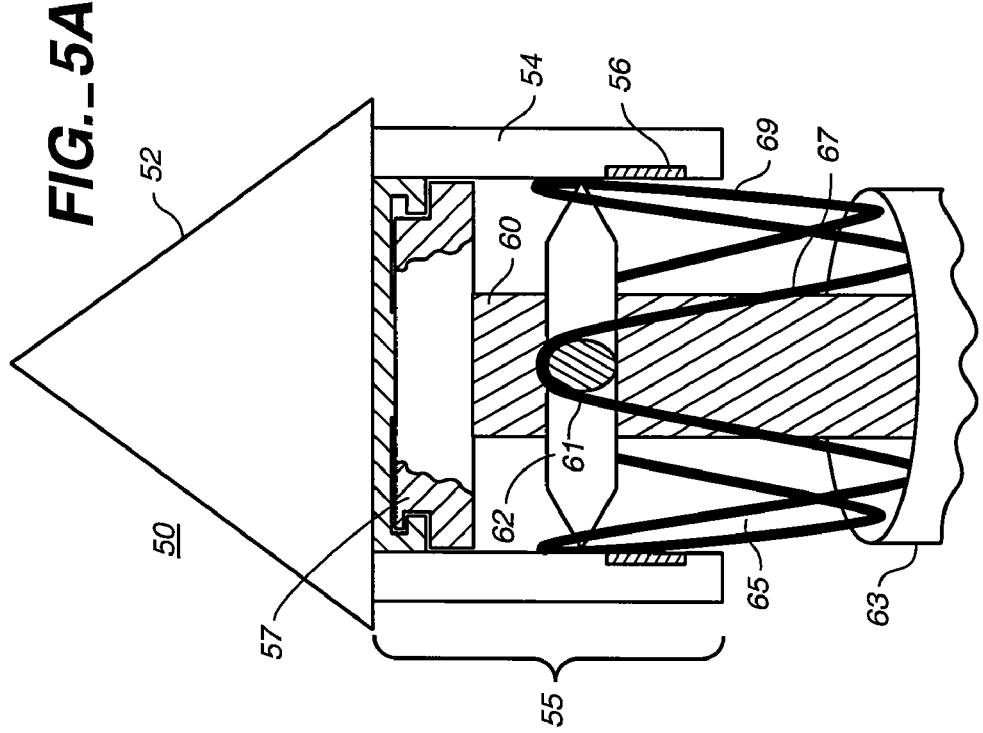
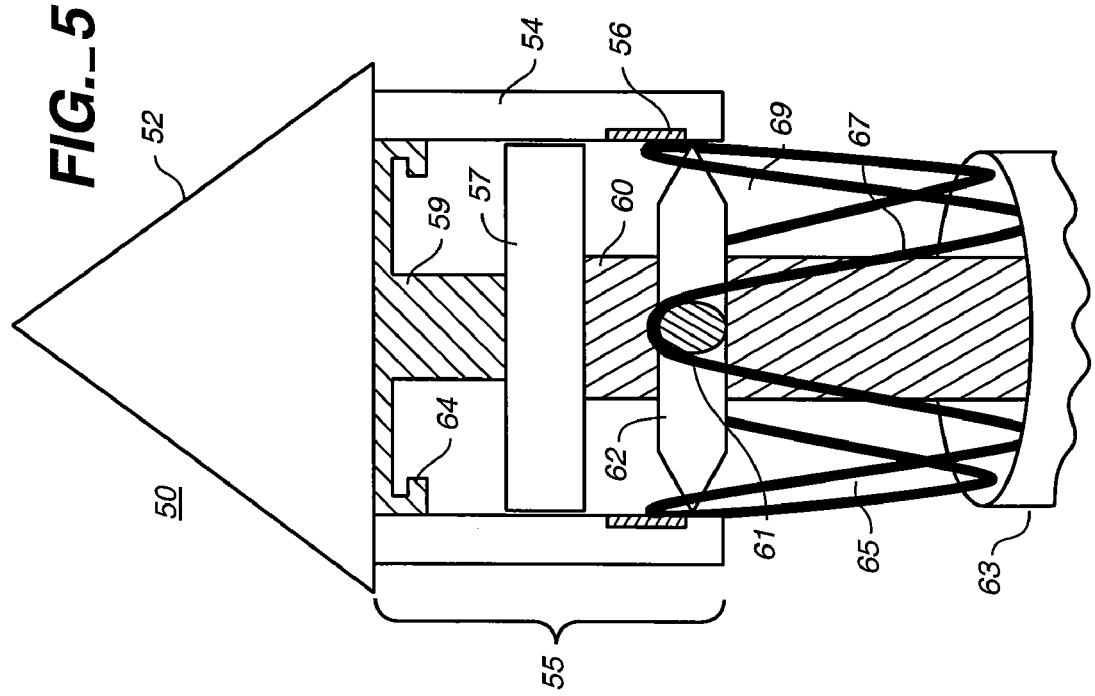

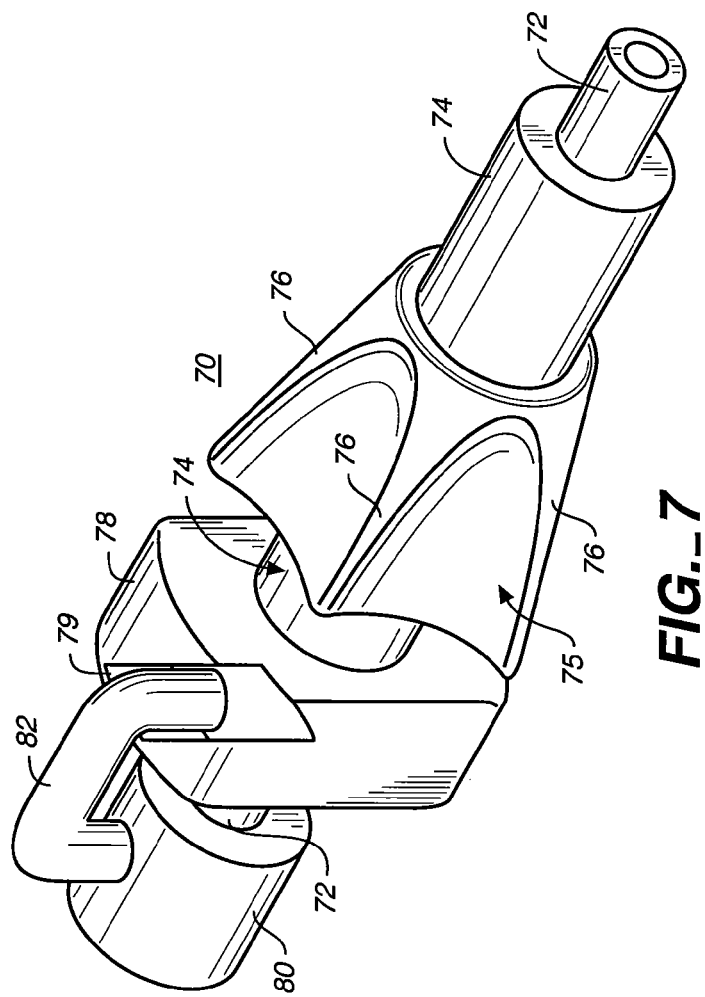
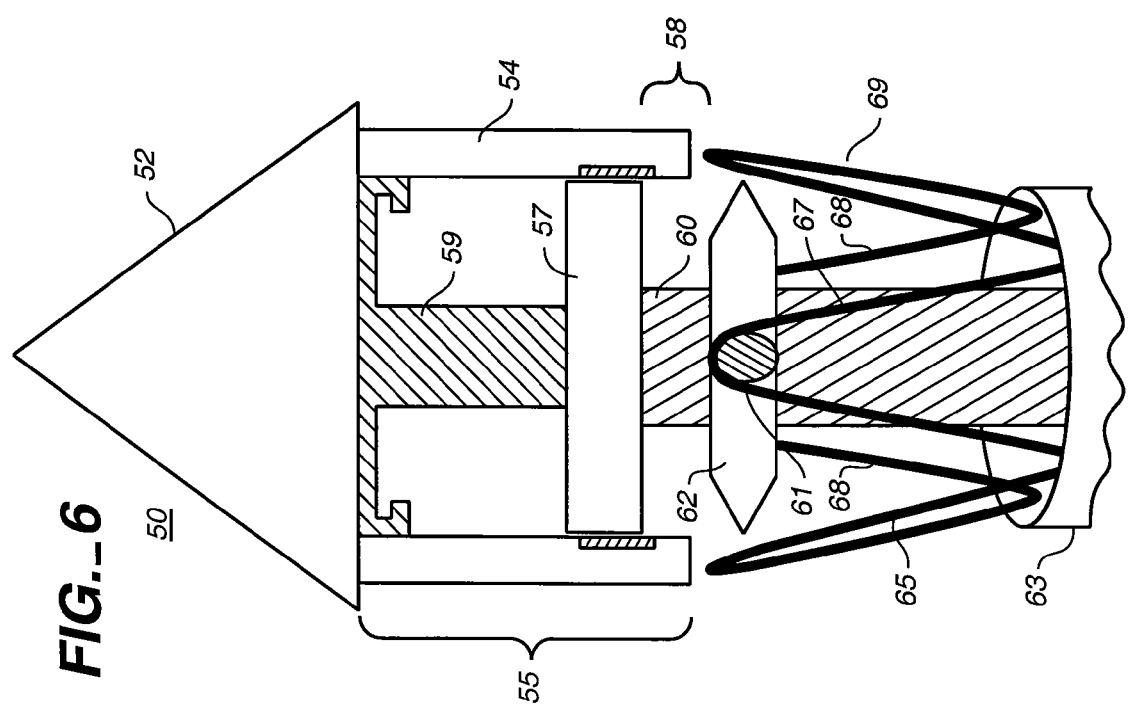

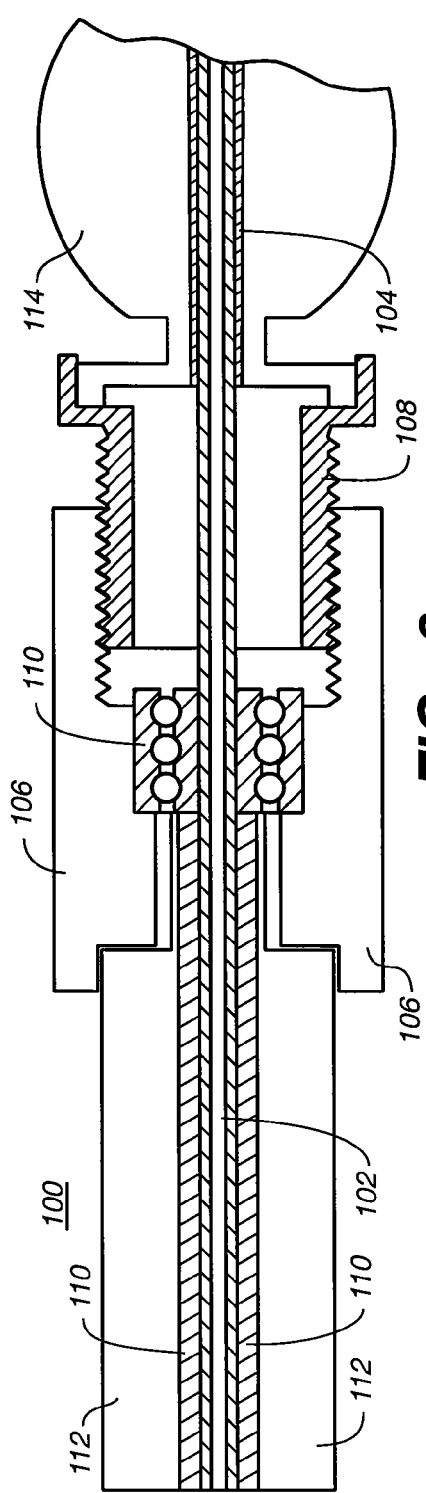
FIG._8
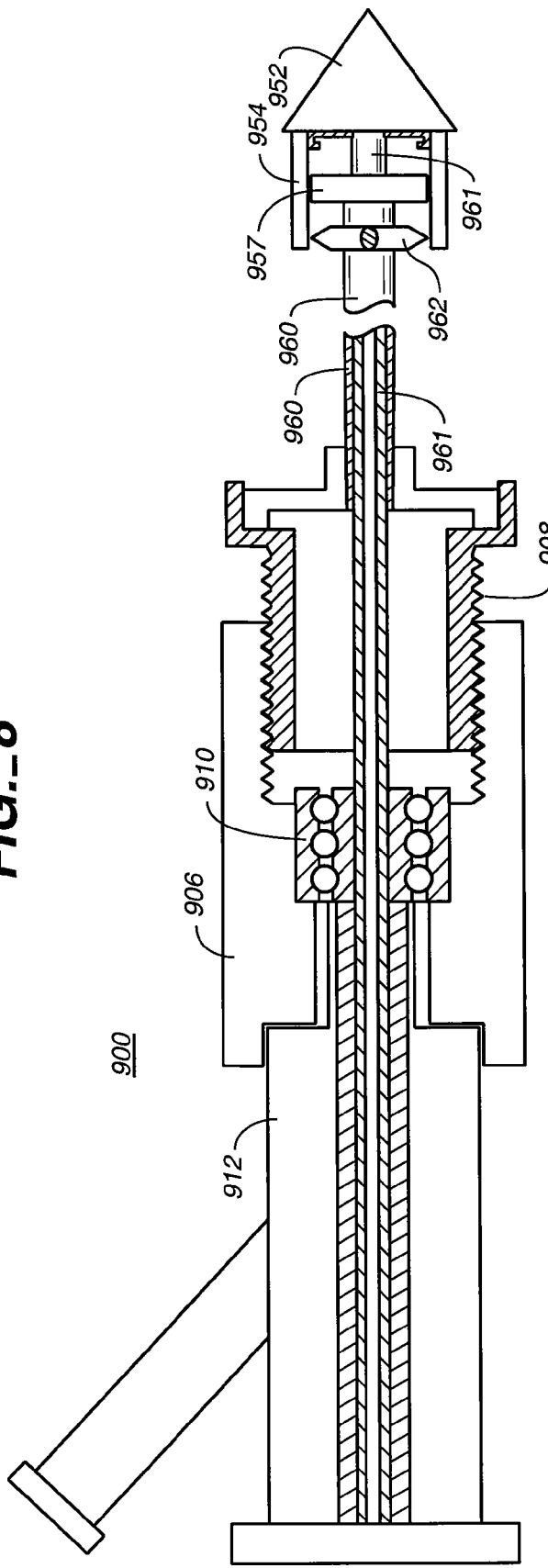
FIG._9

CONTROLLED DEPLOYMENT DELIVERY SYSTEM

RELATED APPLICATION

This application is a continuation from Ser. No. 10/455,978, filed Jun. 5, 2003, which is a continuation in part of provisional application Ser. No. 60/387,278 filed on Jun. 7, 2002 and hereby claims priority therefrom.

FIELD OF THE INVENTION

This invention relates generally to medical devices and procedures, and more particularly to a method and system of deploying a stent-graft in a vascular system.

BACKGROUND OF THE INVENTION

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels. A graft material supported by framework is known as a stent-graft or endoluminal graft. In general, the use of stent-grafts for treatment or isolation of vascular aneurysms and vessel walls which have been thinned or thickened by disease (endoluminal repair or exclusion) are well known. Many stent-grafts, are "self-expanding", i.e., inserted into the vascular system in a compressed or contracted state, and permitted to expand upon removal of a restraint. Self-expanding stent-grafts typically employ a wire or tube configured (e.g. bent or cut) to provide an outward radial force and employ a suitable elastic material such as stainless steel or Nitinol (nickel-titanium). Nitinol may additionally employ shape memory properties. The self-expanding stent-graft is typically configured in a tubular shape of a slightly greater diameter than the diameter of the blood vessel in which the stent-graft is intended to be used. In general, rather than inserting in a traumatic and invasive manner, stents and stent-grafts are preferably deployed through a less invasive intraluminal delivery, i.e., cutting through the skin to access a lumen or vasculature or percutaneously via successive dilatation, at a convenient (and less traumatic) entry point, and routing the stent-graft through the lumen to the site where the prosthesis is to be deployed.

Intraluminal deployment in one example is effected using a delivery catheter with coaxial inner (plunger) and outer (sheath) tubes arranged for relative axial movement. The stent graft is compressed and disposed within the distal end of an outer catheter tube in front of an inner tube. The catheter is then maneuvered, typically routed though a lumen (e.g., vessel), until the end of the catheter (and the stent-graft) is positioned in the vicinity of the intended treatment site. The inner tube is then held stationary while the outer tube of the delivery catheter is withdrawn. The inner tube prevents the stent-graft from moving back as the outer tube is withdrawn. As the outer tube is withdrawn, the stent graft is gradually exposed from a proximal end to a distal end of the stent graft, the exposed portion of the stent-graft radially expands so that at least a portion of the expanded portion is in substantially conforming surface contact with a portion of the interior of the lumen e.g., blood vessel wall. The proximal end of the stent-graft is the end closest to the heart whereas the distal end is the end furthest away from the heart during deployment. In contrast and of note, the distal end of the catheter is usually identified to the end that is farthest from the operator while the proximal end of the catheter is the end nearest the operator. Depending on the access location the stent graft and delivery system description may be consistent or opposite. Logic should prevail to understand the description of an actual systems below.

Many self expanding stent-graft deployment systems are configured to have the proximal end of the stent-graft deploy as the outer tube or sheath is pulled back. The proximal end of the stent-graft is typically designed to fixate and seal the stent graft to the wall of the vessel during deployment. Such a configuration leaves little room for error in placement since re-positioning the stent-graft after initial deployment, except for a minimal pull down retraction, is usually difficult if possible at all. Deploying the proximal end of the stent-graft first makes accurate pre-deployment positioning of the stent-graft critical One attempt to overcome this problem by W. L. Gore utilized a flexible jacket that deploys the stent-graft with a ripcord that opens the jacket along the longitudinal axis of the flexible jacket, e.g., U.S. Pat. No. 6,315,792. Unfortunately, this method introduced a separate non-integrated sheath into the system into the femoral artery and further failed to provide the desired control during deployment. Other stent-graft delivery systems have also attempted to confine the proximal end of the stent-graft, but generally fail to provide adequate control in manipulating the stent-graft positioning in both the initial deployment of the stent graft and the re-deployment of the stent-graft (once the stent-graft has been partially deployed). Another problem encountered with existing systems, particularly with systems that have a distal end of a stent-graft fixed during deployment (or during the uncovering of a sheath) is the frictional forces that can cause the stent-graft to axially compress or bunch up as the sheath is retracted. This bunching increases the density of the stent-graft within the sheath and can further increase the frictional drag experienced during deployment. Thus, a need exists for a method and deployment system that enables partial deployment of a stent-graft while constraining a proximal end of the stent-graft, provides adequate control to enable re-deployment of the stent-graft in various dimensions and further reduces deployment forces during advancement of the stent-graft.

SUMMARY OF THE INVENTION

In a first aspect according to the present invention, a controlled stent-graft deployment delivery system includes a stent-graft, a retractable primary sheath containing the stent-graft in a first constrained diameter configuration, an outer tube within the retractable primary sheath and within the stent-graft, and an inner tube within the outer tube, where the inner tube and the outer tube both move axially relative to the retractable primary sheath and to each other. The system further includes a cap coupled to a distal end of the inner tube and configured to retain at least a portion of a proximal end of the stent-graft in a radially compressed configuration. A controlled relative axial movement between the outer tube and the inner tube releases the proximal end of the stent-graft from the cap and from the radially compressed configuration.

The controlled stent-graft deployment delivery system can have a cap formed from a shroud portion in a flexible tapered tip coupled at the distal end of the inner tube and further include a threaded collar coupled to the inner tube and a mating threaded shaft coupled to the outer tube that enables the relative axial movement between the inner tube and the outer tube for controlled deployment of the stent-graft. The system can further include a proximal lock attached to the outer tube, wherein the stent-graft has a zig zag shaped radially expanding proximal spring at the proximal end of the stent-graft. The apices of the spring at one end remain latched onto the proximal lock in the radially compressed configuration while the spring's end remains captured within the cap. The proximal lock can further include a plurality of ribs or splines for retaining the plurality of apices of the proximal spring of the stent-graft.

In a second aspect according to the present invention, a controlled stent-graft deployment delivery system includes a retractable primary sheath, an outer tube within the retractable primary sheath, an inner tube within the outer tube that can move axially relative to the outer tube, and a cap coupled to a distal end of the inner tube. The system can further include a retention mechanism attached to the outer tube for retaining a proximal end of a stent-graft in a constrained diameter configuration while remaining within the cap while still enabling axial and radial movement of the stent-graft.

In a third aspect according to the present invention, a method for controlled deployment of a stent-graft includes the steps of constraining a proximal end of a stent-graft radially under a cap while partially deploying a remaining portion of the stent-graft, evaluating and adjusting as necessary at least one of the axial and radial positions of the stent-graft after the partial deployment of the remaining portion, and releasing the proximal area of the stent-graft by minimal controlled coaxial movement between the cap and a tube retaining the stent-graft within the cap.

BRIEF DESCRIPTION OF THE DRAWINGS

FIG. 1 is a partial cross sectional view of a stent-graft deployment delivery system without a stent-graft and outer sheath in accordance with the present invention.

FIG. 2 is a close up schematic cross sectional view of the deployment delivery system of FIG. 1 having a stent-graft loaded within an outer sheath.

FIG. 3 is a close up schematic cross sectional view of the deployment delivery system of FIG. 2 showing partial deployment of the proximal portion of the stent graft as proximal end of the stent-graft remains constrained while the distal end of the stent graft remains loaded in its outer sheath.

FIG. 3A is a partial cross sectional view of the stent graft shown in FIG. 3, but without the distal end of the catheter and retaining shaft which is shown in FIG. 3.

FIG. 3B is an oblique view of a stent of the type to be deployed in a delivery mechanism as shown in FIG. 3.

FIG. 4 is a partial cross sectional view of the stent-graft deployment delivery system of FIG. 1 with the proximal end of the stent-graft deployed.

FIG. 5 is a partial cross sectional view of another stent-graft deployment delivery system with a proximal spring crowns constrained within a cap.

FIG. 5A shows a revised position of the end of the stent graft delivery system shown in FIG. 5 where the proximal lock catch is shown engaged with the backplate so that premature release does not occur during shipping and delivery prior to an operator's positioning the stent graft at its intended delivery location.

FIG. 6 illustrates the stent-graft deployment delivery system of FIG. 5 with the plurality of proximal spring crowns released from under the cap.

FIG. 7 illustrates a proximal lock sub-assembly that can be used with a stent-graft deployment delivery system.

FIG. 8 is a cross sectional schematic diagram illustrating a spinning collar actuation assembly used in conjunction with a stent-graft deployment delivery system.

FIG. 9 is a schematic diagram illustrating a stent-graft deployment delivery system in accordance with the present invention.

DETAILED DESCRIPTION

FIGS. 1-4 show portions of a stent-graft deployment delivery system 10. The vertical dashed line provides a reference line to provide correlation between the FIGS. to a common location related to the position of the end spring of the stent graft as elements of the delivery system are manipulated to at first partially deploy and then fully deploy the proximal end of the stent graft 30.

FIG. 1 illustrates the distal tapered tip portion of the delivery system 10 alone without a stent-graft while FIGS. 2-4 show close up views of the deployment delivery system tip portion loaded with a stent-graft 30, with progressive figures showing deployment from within a retractable primary sheath 40. This system could also deploy a stent alone or some other form of endoprosthesis. The subsequent use of "stent-graft" herein should be understood to include other forms of endoprosthesis.

A configuration of the stent-graft deployment system 10 includes a tapered tip 12 that is flexible and able to provide trackability in tight and tortuous vessels. The tapered tip 12 can include a lumen 14 allowing for passage of a guidewire for example. Other tip shapes such as bullet-shaped tips could also be used.

The retractable primary sheath 40 (preferably made of a semi-rigid material such as PTFE) in an un-retracted position contains the stent-graft 30 in a first constrained diameter configuration as shown in FIG. 2. An outer tube 18 is located within the retractable primary sheath 40 and within the stent-graft 30 as shown in FIGS. 1 and 4. An inner tube 20 within the outer tube 18 serves as a guidewire lumen. The inner tube 20 and the outer tube 18 can move along the longitudinal axis relative to each other and can also move along the longitudinal axis relative to the retractable primary sheath. A cap 15 is coupled to a distal area or end portion 11 of the inner tube 20 and is further configured to retain at least a portion of a proximal end of the stent-graft 30 in a radially compressed configuration. Actuating members at the operator's end of the catheter create a relative force in an axial direction to provide a controlled relative axial movement between the outer tube 18 and the inner tube 20 to precisely control the release of the proximal end of the stent-graft (such as proximal springs) from the cap and from the radially compressed configuration.

FIG. 2 illustrates the system 10 with the stent-graft 30 loaded in the delivery system. The stent graft is located within the retractable primary sheath 40 in a pre-deployment un-retracted position.

FIG. 3 illustrates the system 10 with the sheath 40 partially retracted. The proximal end (tip) of the stent-graft 30 is constrained while a proximal portion of the stent-graft 30 (that is now exposed due to the partial retraction of the sheath 40) between the end of the sheath 40 and the constrained proximal end (tip) is partially deployed, which allows longitudinal repositioning of the stent graft before releasing the proximal end (the release of the proximal end of the stent graft prevents repositioning of the stent graft in a direction toward the proximal end of the stent graft, while depending on the degree of expansion and contact between the stent graft and the wall of the vessel in which the stent graft is being deployed, some pull down (movement toward the distal end of the stent graft) of the stent graft is possible.

FIG. 3A is a selected partial schematically consistent view of the phase of stent graft deployment shown in FIG. 3, where the distal end of the catheter and retaining shaft are not included, for clarity. In FIG. 3A the sheath appears to be farther retracted, and the size proportion, while not fully consistent with FIG. 3, is nevertheless schematically consistent. In this figure it can be seen that deployment of the stent graft can be halted and the stent graft repositioned, rotated or moved in either direction axially without great a substantial risk of damaging the walls of the vessel.

In FIG. 4 the proximal end of the stent-graft 30 is shown as having been deployed by the controlled relative axial movement between the inner tube 20 and the outer tube 18. In particular, as shown in FIGS. 1-4, an end cap 15 containing the proximal apices of the end spring of the stent graft can be formed from a shroud portion of the tapered tip 12 which is coupled to the distal end of the outer tube 18. Within the shroud portion (formed by tubular body portion 16 of the tapered tip 12) preferably resides a back plate 17 coupled to a distal portion or end of the outer tube 18 that serves as a proximal stop for the stent-graft 30. The tubular body portion 16 of the shroud portion may also include a support (reinforcing) ring 13 near the proximal end of the tapered tip 12 to provide additional rigidity to the cap and prevents the cap shroud portion 16, which is preferably made of a plastic material from stretching (or distorting) in diameter. This configuration thereby prevents premature release of the of the proximal end of the stent graft constrained by the cap (premature stretching could create a gap large enough for the restrained members of the stent graft to spring loose. Additionally, a proximal lock (retainer) 22 is also coupled to a distal portion of the outer tube 18. The proximal lock 22 preferably includes at least one or a plurality of ribs (or splines) 23 that can together with the shroud portion 16 serve as an axial constraint for the end stent-graft 30. The proximal end (or the proximal springs 31, 32, and 33) of the stent-graft 30 cannot deploy until the proximal end of the ribs of the proximal lock clear the end of the shroud portion 16 of the tip.

A stent-graft can include a polyester or Dacron material (forming the graft material 34 (FIG. 3B)) sewn to a Nitinol support structure 35 using polyester sutures. In one example, a Nitinol wire is used to form a skeletal structure 35 that provides support, strength and stability to the stent-graft. The stent-graft can also have a support member (crown stent or spring 36) on the proximal end of the stent-graft that is left mainly uncovered by the graft material. The uncovered portion will typically have a zig zag like pattern with a predetermined number of apices protruding up. The apices form the extreme end of what is known as the proximal spring (or crown spring 36) of the stent-graft.

As shown in FIGS. 1-3, the gap 19 between the backplate 17 and the proximal lock 22 is preferably designed to hold the protruding apices of the proximal spring. The apices straddle the ribs 23 of the proximal lock 22 and remain trapped between the back plate and the proximal lock until the relative movement between the outer tube 18 and the inner tube 20 exposes the gap 19 and releases the apices 31-33 of the proximal spring as shown in FIG. 4. In other words, the apices 31-33 cannot release from the ribs 23 on the proximal lock 22 while the apices remain within the shroud portion 15. When the inner tube 20 and tapered tip 12 assembly are advanced forward exposing the proximal lock 22, the apices of the proximal spring release from the respective ribs 23 of the proximal lock 22. The release results in the deployment of the proximal end of the stent-graft 30 as shown in FIG. 4. Note that while the apices of the proximal spring remain in gap 19 and within the cap or shroud portion of the tapered tip 12, the whole of the proximal spring remains axially (longitudinally) constrained as well as radially constrained. The support ring 13, usually made of metal, helps prevent the radial force of the proximal springs from distorting the shape of the tapered tip and particularly the shroud portion of the tapered tip.

Close up schematic plan views of another stent-graft deployment delivery system 50 are shown in FIGS. 5 and 6. FIG. 5 illustrates a plurality of proximal spring apices 65, 67 and 69 (68 is hidden in this view) of a stent-graft 63 constrained within a cap or shroud portion 55 of a tip 52. The cap or shroud portion 55 can be formed from the tube section 54 which can further include support ring 56.

FIG. 5A illustrates the backplate 57 in engagement with the inner tube assembly's proximal lock catch 64. The proximal lock catch 64 is a plate or bar which spans the end of the backplate 57 and has two engagement hooks to engage with engagement hook receiving slots or channels in the backplate 57. Two offset partial cross sectional views of these slots or channels can be seen on the right and left sides of the backplate 57 shown in FIG. 5A. The left side shows the left side protrusion from the lock catch 64 engaged in the slot and prevented from release by a slot lip, while the right side shows an angularly offset cross section (not diametrically opposite the left side) where the slot or channel is open and the slot lip is absent. The release of the catch 64 from engagement with the backplate, can be performed by a rotational motion by having an obliquely shaped slot similar to the channel as more precisely pictured in FIG. 7, below. Or by initiating a relative rotational motion between the inner and outer tubes. While the proportions shown in the Figures are not consistent with the type of arrangement shown in FIG. 7, a person skilled in the art will recognize the schematic nature of the items presented in FIGS. 5, 5A, and 6, and understand that the proportions can be changed to include the functional engagement and disengagement action between the inner and outer tubes as presented and discussed for FIG. 7.

FIG. 6 illustrates another close up view of the stent-graft deployment delivery system 50 with the plurality of proximal spring apices 65, 67, 69 and 68 released from under the cap. As in system 10 described in FIGS. 1-4, the stent-graft deployment delivery system 50 includes an outer tube 60 coupled to both a backplate 57 and a proximal lock 62 having a plurality of ribs 61, an inner tube 59 (within the outer tube 60) coupled to the tip 52, and a proximal lock catch 64 connected to the tip 52. When the inner tube 59 and tip 52 to which it is fixed are advanced forward exposing the proximal lock 62, the apices 65, 67, 69 and 68 of the proximal spring are release from the respective ribs (e.g., 61) of the proximal lock 62. The release results in the deployment of the proximal end of the stent-graft 63 as shown in FIG. 6.

While the apices 65, 67, 69 and 68 of the proximal spring are held in the gap between the backplate and proximal lock and within the cap or shroud portion of the tapered tip 52, the whole of the proximal spring remains axially constrained as well as radially constrained. The support ring 56, as previously explained helps prevent the radial force of the proximal springs from distorting the shape of the tip and particularly the shroud portion of the tip.

Now referring to FIG. 7, a perspective view of a proximal lock assembly 70 is shown including an inner tube 72 within an outer tube 74, a proximal lock 75, a backplate 78 and a proximal lock catch 80. The inner tube 72 is attached to the proximal lock catch 80 at a distal end of the inner tube 72. The proximal lock catch 80 can be connected to a tip of a stent-graft delivery system as previously shown schematically in FIGS. 5 and 6. The inner tube 72 further serves as a guidewire (not shown) lumen. The backplate 78 is attached at a distal end of the outer tube 74 with the proximal lock 75 being attached near the distal end of the outer tube 74 as shown. The backplate 78 serves as a proximal stop (preventing the stent graft from moving with the shroud and tip assembly when the shroud (cap) is moved forward to release the apices of the proximal spring) for a stent-graft (not shown) and preferably includes at least one channel 79. The proximal lock catch 80 can include at least one post 82 that rides in the channel 79 (disposed at an oblique angle with respect to the longitudinal axis of the stent graft and catheter, the channel (slot) being closed at the proximal end and open at the opposite end) of the backplate 78. With this arrangement, the proximal lock 75 cannot separate from the tip (and catch 80) (because of the closed proximal end of the channel) until the post or posts 82 are moved distally so that the end(s) of the posts (e.g., 82) are expelled from and clear the end of the channel or channels 79 so they no longer prevent proximal motion of the tip relative to the proximal lock 75. To release the catch 80, the proximal lock 75 and tip (or catch 80) must be forced together (or compressed) (the actuation mechanism actually has to be moved (turned) in the opposite direction to motion used for normal deployment), which is opposite the force that is provided during the normal deployment motion (a separation force). The clearing is accomplished by pulling (using the threaded deployment relative motion mechanism of the catheter described below) the inner tube 72 axially with respect to the outer tube so that the post 82 is forced out of the channel in the backplate and completely disengages (or escapes) the channel 79 in the backplate 78. Once a user compresses the tip (or catch 80) and proximal lock 75 releasing the catch 80 from the backplate 78, the proximal lock can be advanced out of the shroud portion of the tip. The distal mechanism for actuating the relative coaxial movement of the inner tube 72 and outer tube 74 (and the respective components of the assembly 70 respectively attached thereto) will become apparent with the description of FIGS. 8 and 9. Such an assembly prevents premature deployment and reduces the likelihood of an unintentional deployment of a stent-graft. This arrangement also prevents any elongation forces the deployment system could experience during tracking and/or deployment which could cause premature deployment.

The proximal lock 75 preferably includes a number of contoured ribs 76 about the periphery of the proximal lock 75. The number of ribs will ideally depend on the number of apices in a proximal spring of a stent-graft (not shown) although the present invention is not necessarily limited thereto. The contouring of the ribs 76 aid in the loading of the apices of the proximal spring onto the proximal lock (by providing an inclined surface such that a proximal end spring constrained in a fixture to a cylindrical shape can be mounted over the thin diameter end of the contour and then forced toward the wide end so that the contoured shape proximal lock is acting as an expansion mandrel, allowing the apices of the proximal spring to be forced past the wide end and be engaged by the end of the contoured splines, then the shroud can be introduced over the now proximal lock engaged apices of the proximal spring of the stent graft) and the wide end of the contoured splines further providing an axial constraint for the proximal end of the stent-graft until deployment when the proximal lock clears the shroud section of the tip as previously explained with respect to FIGS. 1-6. The relative movement between the inner tube 72 and the outer tube 74 will cause the release of the proximal end (proximal springs) of the stent-graft. The contoured surface of the proximal lock also provides an advantage after the proximal end of the stent graft is released and the stent graft is fully deployed, such that the taper of the outer surface makes it easier to retract the catheter tip back into the sheath, the contoured outer surface once the small diameter end begins access to the end of the sheath, acts as a guide to channel the sheath to coaxially surround the tip, so that contact and damage to vascular internal surfaces is minimized as the tip is retracted within the sheath.

Now referring to FIG. 8, a schematic diagram of a distal assembly or a spinning collar actuation assembly 100 is shown illustrating the controlled relative axial movement of an inner tube (e.g., 102) to an outer tube (e.g., 104). The assembly 100 preferably includes a luer 112 and spindle 110 attached to the inner tube (e.g., 102), a threaded shaft 108 and handle 114 coupled to the outer tube (e.g., 104), and a collar 106. The collar 106 can be attached to the inner tube (e.g., 102) and yet also spin in relation to the luer 112. In this configuration, the inner tube 102 can advance axially in relation to the outer tube 104 by screwing or spinning the collar 106 down or across the threaded shaft 108. The threaded shaft 108 can be similar to the threaded portion of a Touchy Borst connector commonly used in catheters. The assembly 100 provides a simple mechanism by twisting or spinning for release (or activation) of the apices of or the proximal spring of a stent graft during deployment.

A schematic diagram of a stent-graft deployment delivery system 900 including a tip 952 (coupled to an inner tube 961) having a cap or shroud portion formed from a tube section 954, an outer tube 960 coupled to both a backplate 957 and a proximal lock 962, as well as a distal assembly or a spinning collar actuation assembly is shown in FIG. 9. The distal assembly provides controlled relative axial movement of the inner tube 961 with respect to the outer tube 960 and preferably includes a luer 912 and spindle 910 attached to the inner tube 961, a threaded shaft 908 coupled to the outer tube 960, and a collar 906. The collar 906 can be attached to the inner tube 961 and yet also spin in relation to the luer 912. In this configuration, the inner tube 961 can advance axially in relation to the outer tube 960 by screwing or spinning the collar 906 down or across the threaded shaft 908. Note that a sheath and stent-graft are not shown in FIGS. 8 and 9 and the sheath and it actuation mechanism and handle (not shown) are located around the inner and outer tubes as previously described between the stent graft proximal spring apices actuation handle (mechanism) and the tip of the catheter where the stent graft is deployed.

When treating Abdominal Aortic Aneurisms (AAA), for example, there are several anatomical challenges when advancing a stent-graft deployment system or device and appropriately placing the stent-graft itself. A major challenge is encountered in the region of the aortic bifurcation (this typically includes the femoral, external iliac, and common iliac arteries). Existing stent-graft delivery systems that deploy from a distal end of the stent-graft fail to provide sufficient options for re-alignment once the stent-graft is even partially deployed. Existing stent-graft delivery systems that deploy from a proximal end of the stent-graft fail to provide adequate control in the eventual release of the proximal end of the stent-graft. Stent-grafts that require alignment of ports with branch arteries can use the re-deployment capabilities and the controlled release mechanisms of the present invention to a great advantage. Since the system of the present invention constrains the proximal end of the stent-graft radially while allowing the middle and/or distal portions of the stent-graft to deploy first, the stent-graft can be repositioned both axially and radially by preventing the stent-graft from fixating itself to a vessel, even when partially deployed.

Stent-grafts that require alignment with branch arteries can have the middle or port areas of the stent-graft release first. The stent-graft can be realigned so that all ports are properly aligned before releasing the proximal end of the stent-graft. The proximal end of the stent-graft is also axially constrained which enables the delivery system to maintain the position of the stent-graft during the full deployment sequence event if the stent-graft has little or no axial support. Since the present invention fixes the proximal end of the stent-graft during deployment while the sheath is withdrawn, the frictional forces between the stent-graft and sheath cause the stent-graft to be held under a tensile load. While under a tensile load, the density of the stent-graft and the compressive forces within the sheath are reduced. Additionally, using the design of the present invention, deployment forces can be further reduced by removing supports (such as connecting bars) in the stent-graft since such supports would no longer be needed for deployment.

Additionally, the description above is intended by way of example only and is not intended to limit the spirit and scope of the invention and it equivalent as understood by persons skilled in the art.

What is claimed is:

1. A controlled stent-graft deployment delivery system, comprising:
   a stent-graft;
   a retractable primary sheath containing said stent-graft in a first constrained diameter configuration;
   an outer tube within the retractable primary sheath and within the stent-graft;
   an inner tube within the outer tube, wherein the inner tube and the outer tube both axially can move relative to the retractable primary sheath and to each other;
   a retention mechanism configured to retain at least a portion of a proximal portion of the stent-graft in a radially compressed configuration after said primary sheath has been retracted, wherein a controlled relative axial movement between the outer tube and the inner tube releases the proximal end of the stent-graft from the retention mechanism and from the radially compressed configuration, the retention mechanism comprising:
   a proximal lock attached to said outer tube, said proximal lock comprising ribs; and
   a cap attached to said inner tube, said cap comprising a shroud, wherein proximal spring apices at the proximal end of said stent-graft remain latched on said ribs in the radially compressed configuration while the proximal spring apices remain within the shroud.

2. The controlled stent-graft deployment delivery system of claim 1, wherein a threaded collar coupled to the inner tube and a mating threaded shaft coupled to the outer tube enables the relative axial movement between the inner tube and the outer tube for controlled deployment of the stent-graft.

3. The controlled stent-graft deployment delivery system of claim 1, wherein the plurality of ribs are each tapered to aid in the process of re-introducing the proximal lock into the retractable primary sheath after deployment of the stent-graft.

4. A controlled stent-graft deployment delivery system, comprising:
   a retractable primary sheath;
   an outer tube within the primary sheath, wherein the outer tube is within a stent-graft;
   an inner tube within the outer tube, wherein the inner tube can move axially relative to the outer tube; and
   a retention mechanism including splines attached to said outer tube and a cap attached to said inner tube retaining a proximal end of a stent-graft in a constrained diameter configuration while proximal spring apices at a proximal end of the stent graft are still located latched on said splines and captured by said cap while still enabling axial and radial movement of the stent-graft.

5. The controlled stent-graft deployment delivery system of claim 4, wherein the retention mechanism enables a partial deployment of a remaining distal portion of the stent-graft while maintaining the proximal end of the stent-graft in the constrained diameter configuration.

6. A method for controlled deployment of a stent-graft, comprising the steps of:
   constraining a proximal end of a stent-graft radially to a distal end of a delivery mechanism by having proximal springs at a proximal end of the stent graft latched and captured on splines at a distal end of a delivery system while partially deploying a remaining portion of the stent-graft comprising the step of constraining proximal springs of the stent-graft between a shroud and splines of said distal end of said delivery mechanism, the constraining comprising latching said proximal springs on said splines with said shroud, said splines being attached to an outer tube, said shroud being attached to an inner tube, the partially deploying comprising retracting a primary sheath containing said stent graft relative to said outer tube and said inner tube;
   adjusting at least one of the axial and radial positions of the stent-graft after the partial deployment the remaining portion; and
   releasing the proximal area of the stent-graft by controlled coaxial relative movement between the inner tube and the outer tube to release the proximal springs from said splines; wherein the inner tube is within the outer tube and the outer tube is within the stent-graft.

* * * * *